United States Patent [19]
Saadat et al.

[11] Patent Number: 6,051,008
[45] Date of Patent: *Apr. 18, 2000

[54] APPARATUS HAVING STABILIZATION MEMBERS FOR PERCUTANEOUSLY PERFORMING SURGERY AND METHODS OF USE

[75] Inventors: Vahid Saadat, Redwood Shores; John H. Ream, San Jose, both of Calif.

[73] Assignee: AngioTrax, Inc., Sunnyvale, Calif.

[ * ] Notice: This patent is subject to a terminal disclaimer.

[21] Appl. No.: 09/213,089

[22] Filed: Dec. 15, 1998

Related U.S. Application Data

[63] Continuation-in-part of application No. 08/863,877, May 27, 1997, Pat. No. 5,910,150.

[51] Int. Cl.[7] .................................................... A61B 17/00
[52] U.S. Cl. .............................. 606/159; 606/170; 606/7; 606/15
[58] Field of Search ................................ 606/1, 159, 170, 606/171, 180, 181, 45–49, 7, 15; 604/22

[56] References Cited

U.S. PATENT DOCUMENTS

| | | |
|---|---|---|
| Re. 33,258 | 7/1990 | Onik et al. . |
| 3,557,794 | 1/1971 | VanPatten . |
| 4,362,161 | 12/1982 | Reimels et al. . |
| 4,576,162 | 3/1986 | McCorkle . |
| 4,582,056 | 4/1986 | McCorkle . |
| 4,640,296 | 2/1987 | Schnepp-Pesch et al. . |
| 4,646,738 | 3/1987 | Trott . |
| 4,729,763 | 3/1988 | Henrie . |
| 4,813,930 | 3/1989 | Elliott . |
| 4,895,166 | 1/1990 | Farr et al. . |
| 4,923,462 | 5/1990 | Stevens . |
| 4,976,710 | 12/1990 | Mackin . |
| 5,093,877 | 3/1992 | Aita et al. . |
| 5,104,393 | 4/1992 | Isner et al. . |
| 5,106,386 | 4/1992 | Isner et al. . |
| 5,152,744 | 10/1992 | Krause et al. . |
| 5,242,460 | 9/1993 | Klein et al. . |

(List continued on next page.)

FOREIGN PATENT DOCUMENTS

| | | |
|---|---|---|
| 0868 923A2 | 7/1998 | European Pat. Off. . |
| 0876 796A2 | 11/1998 | European Pat. Off. . |
| 0895 752A1 | 10/1999 | European Pat. Off. . |
| WO96/26675 | 9/1996 | WIPO . |
| WO98/05307 | 2/1998 | WIPO . |
| WO98/38916 | 9/1998 | WIPO . |
| WO98/39045 | 9/1998 | WIPO . |

(List continued on next page.)

OTHER PUBLICATIONS

Cooley, Denton A., M.D. et al., "Transmyocardial Laser Revascularization: Anatomic Evidence of Long–Term Channel Patency," *Texas heart Institute Journal*, vol. 21, No. 3 (1994), pp. 220–224.

Cooley, Denton A., M.D. et al., "Transmyocardial Laser Revascularization: Clinical Experience with Twelve–Month Follow–Up," *The Journal of Thoracic and Cardiovascular Surgery*, (Apr. 1996), pp. 791–799.

(List continued on next page.)

*Primary Examiner*—Gary Jackson
*Assistant Examiner*—William Lewis
*Attorney, Agent, or Firm*—Fish & Neave; Nicola A. Pisano

[57] ABSTRACT

Apparatus and methods for performing surgery within an organ or vessel are provided. A catheter is provided having a longitudinal axis and an end region carrying an end effector, the end region movable to a series of positions along the longitudinal axis and with an selectable orientation relative to the longitudinal axis. The catheter includes elements for stabilizing the end region of the apparatus within an organ or vessel, and for counteracting reaction forces developed during actuation of the end effector.

22 Claims, 10 Drawing Sheets

U.S. PATENT DOCUMENTS

| | | |
|---|---|---|
| 5,281,218 | 1/1994 | Imran . |
| 5,285,795 | 2/1994 | Ryan et al. . |
| 5,323,781 | 6/1994 | Ideker et al. . |
| 5,324,284 | 6/1994 | Imran . |
| 5,330,466 | 7/1994 | Imran . |
| 5,336,237 | 8/1994 | Chin et al. . |
| 5,342,300 | 8/1994 | Stefanadis et al. . |
| 5,354,310 | 10/1994 | Garnic et al. . |
| 5,358,472 | 10/1994 | Vance et al. . |
| 5,358,485 | 10/1994 | Vance et al. . |
| 5,379,772 | 1/1995 | Imran . |
| 5,380,316 | 1/1995 | Aita et al. . |
| 5,383,884 | 1/1995 | Summers . |
| 5,389,073 | 2/1995 | Imran . |
| 5,389,096 | 2/1995 | Aita et al. . |
| 5,403,334 | 4/1995 | Evans et al. . |
| 5,409,000 | 4/1995 | Imran . |
| 5,415,166 | 5/1995 | Imran . |
| 5,439,474 | 8/1995 | Li . |
| 5,443,443 | 8/1995 | Shiber . |
| 5,465,717 | 11/1995 | Imran et al. . |
| 5,488,958 | 2/1996 | Topel et al. . |
| 5,497,784 | 3/1996 | Imran . |
| 5,505,725 | 4/1996 | Samson . |
| 5,507,802 | 4/1996 | Imran . |
| 5,520,634 | 5/1996 | Fox et al. . |
| 5,527,279 | 6/1996 | Imran . |
| 5,554,152 | 9/1996 | Aita et al. . |
| 5,562,694 | 10/1996 | Sauer et al. . |
| 5,569,178 | 10/1996 | Henley . |
| 5,569,284 | 10/1996 | Young et al. . |
| 5,575,772 | 11/1996 | Lennox . |
| 5,575,787 | 11/1996 | Abela et al. . |
| 5,578,067 | 11/1996 | Ekwall et al. . |
| 5,591,159 | 1/1997 | Taheri . |
| 5,601,573 | 2/1997 | Fogelberg et al. . |
| 5,601,586 | 2/1997 | Fucci et al. . |
| 5,601,588 | 2/1997 | Tonomura et al. . |
| 5,607,421 | 3/1997 | Jeevanandam et al. . |
| 5,609,591 | 3/1997 | Daikuzono . |
| 5,609,621 | 3/1997 | Bonner . |
| 5,611,803 | 3/1997 | Heaven et al. . |
| 5,643,253 | 7/1997 | Baxter et al. . |
| 5,651,781 | 7/1997 | Grace . |
| 5,662,124 | 9/1997 | Wilk . |
| 5,662,671 | 9/1997 | Barbut et al. . |
| 5,669,920 | 9/1997 | Conely et al. . |
| 5,683,362 | 11/1997 | Rowland et al. . |
| 5,724,975 | 3/1998 | Negus et al. . |
| 5,725,521 | 3/1998 | Mueller . |
| 5,782,823 | 7/1998 | Mueller . |
| 5,807,384 | 9/1998 | Mueller . |
| 5,830,210 | 11/1998 | Rudko et al. . |
| 5,830,222 | 11/1998 | Makower . |
| 5,840,059 | 11/1998 | March et al. . |
| 5,871,495 | 2/1999 | Meuller . |
| 5,893,848 | 4/1999 | Negus et al. . |
| 5,910,150 | 6/1999 | Saadat .................................. 606/159 |

OTHER PUBLICATIONS

Frazier, O.H., M.D., "Myocardial Revascularization With Laser: Preliminary Findings," *Supplement II Circulation,* vol. 92, No. 9, (Nov. 1995), pp. II–58–II–65.

Hardy, Roger Ian, "A Histologic Study of Laser–Induced Transmyocardial Channels," *Lasers in Surgery and Medicine,* (1987), pp. 6:563–573.

Hershey, John E. et al., "Transmyocardial Puncture Revascularization: A Possible Emergency Adjunct to Arterial Implant Surgery," *Geriatrics,* (Mar. 1969), pp. 101–108.

Horvath, Keith A., M.D., et al., "Recovery and Viability of an Acute Myocardial Infarct After Transmyocardial Laser Revascularization," *Journal of American College of Cardiology,* vol. 25, No. 1 (Jan. 1995), pp. 258–263.

Horvath, Keith A., M.D., et al., "Transmyocardial Laser Revascularization: Operative Techniques and Clinical Results at Two Years," *The Journal of Thoracic and Cardiovascular Surgery,* (May 1996) pp. 1047–1053.

"PMR Poduct, Axcis™ PMR™ System," http://www.cardiogenesis.com/percutaneous/product.html, Jan. 27, 1999.

"The PMR™ Procedure," http://www.cardiogenesis.com/percutaneous/procedure.html, Jan. 27, 1999.

Kohmoto, Takushi, M.D., "Does Blood Flow Through Holmium: YAG Transmyocardial Laser Channels?," *Ann. Thorac. Surg.,* (1996) pp. 61: 861–868.

Lee, Garrett, M.D., "Effects of Laser Irradiation Delivered by Flexible Fiberoptic System on the Left Ventricular Internal Myocardium," *American Heart Journal,* (Sep. 1983), pp. 587–590.

NASA's Jet Propulsion Laboratory, "Swivel–Head Sampling Drill Bit," *NASA Tech Briefs,* Nov. 1998.

Sen, P.K. et al., "Further Studies in Multiple Transmyocardial Acupuncture as a Method of Myocardial Revascularization," *Surgery,* vol. 64, No. 5, (Nov. 1968), pp. 861–870.

Thaning, Otto, "Transmyocardial Laser Revascularisation in South Africa," *SAMJ,* vol. 85, No. 8 (Aug. 1995) pp. 787–788.

Von Oppell, Ulrich O., "Transmyocardial Laser Revascularisation," *SAMJ,* vol. 85, No. 9, (Sep. 1995), p. 930.

White, Manuel et al., "Multiple Transmyocardial Puncture Revascularization in Refractory Ventricular Fibrillation due to Myocardial Ischemia," *The Annals of Thoracic Surgery,* vol. 6, No. 6, (Dec. 1968), pp. 557–563.

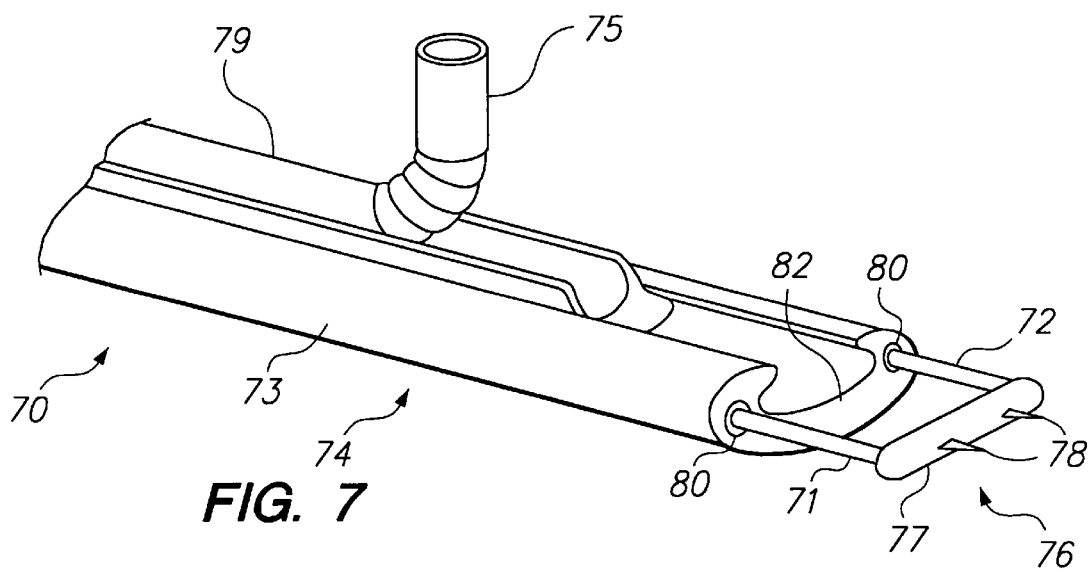
FIG. 7
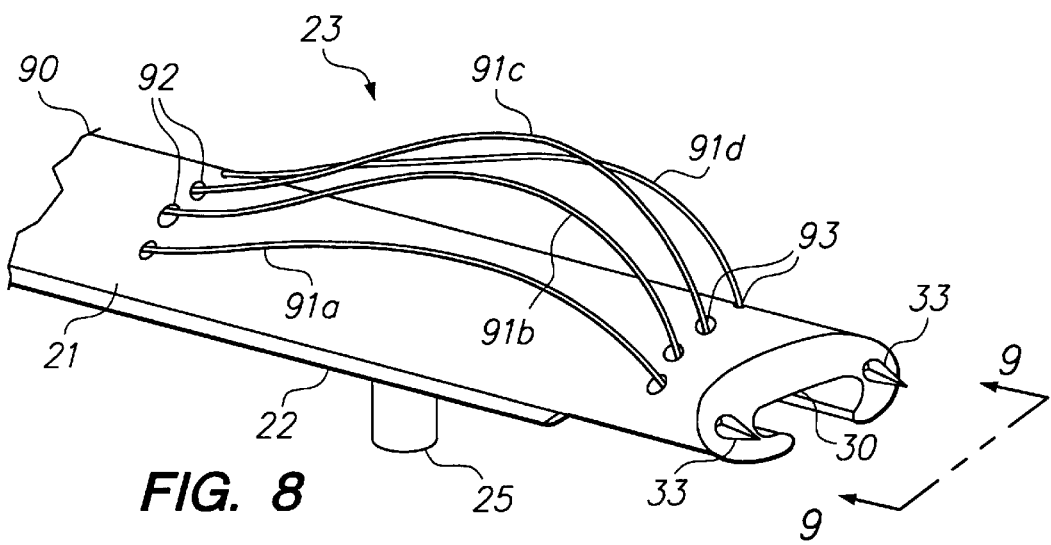
FIG. 8
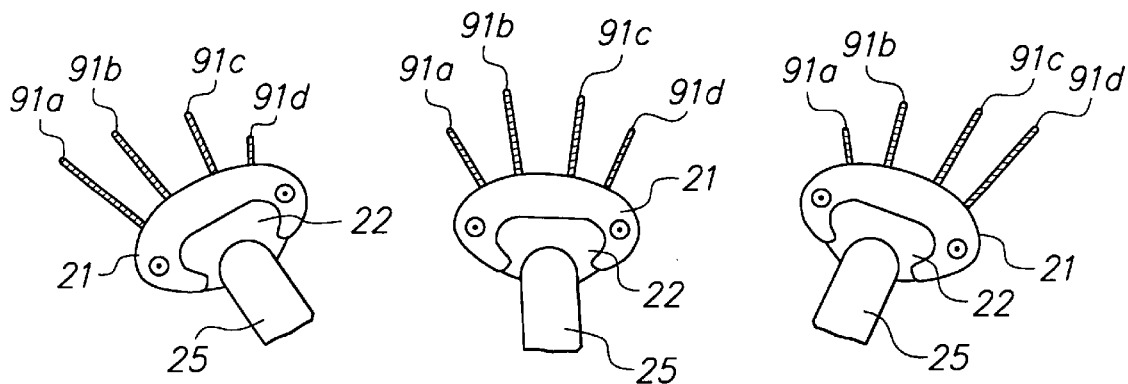
FIG. 9A   FIG. 9B   FIG. 9C

APPARATUS HAVING STABILIZATION MEMBERS FOR PERCUTANEOUSLY PERFORMING SURGERY AND METHODS OF USE

REFERENCE TO RELATED APPLICATIONS

The present application is a continuation-in-part application of commonly assigned U.S. patent application Ser. No. 08/863,877, filed May 27, 1997, now U.S. Pat. No. 5,910,150.

FIELD OF THE INVENTION

The present invention relates to apparatus and methods for performing surgery on an interior wall of a hollow-body organ such as the heart, or within the brain cavities and the like. More particularly, the present invention provides a device that enables a clinician to perform surgery on an interior wall of an organ or vessel using apparatus for stabilizing an end effector during the surgery.

BACKGROUND OF THE INVENTION

A leading cause of death in the United States today is coronary artery disease, in which atherosclerotic plaque causes blockages in the coronary arteries, resulting in ischemia of the heart (i.e., inadequate blood flow to the myocardium). The disease manifests itself as chest pain or angina. In 1996, approximately 7 million people suffered from angina in the United States.

Coronary artery bypass grafting (CABG), in which the patient's chest is surgically opened and an obstructed artery replaced with a native artery harvested elsewhere, has been the conventional treatment for coronary artery disease for the last thirty years. Such surgery creates significant trauma to the patient, requires long recuperation times, and causes a great deal of morbidity and mortality. In addition, experience has shown that the graft becomes obstructed with time, requiring further surgery.

More recently, catheter-based therapies such as percutaneous transluminal coronary angioplasty (PTCA) and atherectomy have been developed. In PTCA, a mechanical dilatation device is disposed across an obstruction in the patient's artery and then dilated to compress the plaque lining the artery to restore patency to the vessel. Atherectomy involves using an end effector, such as a mechanical cutting device (or laser) to cut (or ablate) a passage through the blockage. Such methods have drawbacks, however, ranging from re-blockage of dilated vessels with angioplasty to catastrophic rupture or dissection of the vessel during atherectomy. Moreover, these methods may only be used for that fraction of the patient population where the blockages are few and are easily accessible. Neither technique is suitable for the treatment of diffuse atherosclerosis.

A more recent technique, which holds promise of treating a larger percentage of the patient population, including those patients suffering from diffuse atherosclerosis, is referred to as transmyocardial revascularization (TMR). In this method, a series of channels are formed in the left ventricular wall of the heart. Typically, between 15 and 30 channels about 1 mm in diameter and up to 3.0 cm deep are formed with a laser in the wall of the left ventricle to perfuse the heart muscle with blood coming directly from the inside of the left ventricle, rather than traveling through the coronary arteries. Apparatus and methods have been proposed to create those channels both percutaneously and intraoperatively (i.e., with the chest opened).

U.S. Pat. No. 5,389,096 to Aita et al. describes a catheter-based laser apparatus for percutaneously forming channels extending from the endocardium into the myocardium. U.S. Pat. No. 5,380,316 to Aita et al. describes an intraoperative laser-based system for performing TMR. U.S. Pat. No. 5,591,159 to Taheri describes a mechanical apparatus for performing TMR involving a catheter having an end effector formed from a plurality of spring-loaded needles.

Neither the Aita nor Taheri devices describe apparatus wherein the laser-tip or spring-loaded needles are stabilized during the channel-forming process. Because the end effector of such devices may shift position while in use, such previously known devices may not provide the ability to reliably determine the depth of the channels, nor the relative positions between channels if multiple channels are formed.

In view of the shortcomings of previously known TMR devices, it would be desirable to provide apparatus and methods for performing percutaneous surgery, such as TMR, that permit precise control of the end region of the device carrying the end effector.

It also would be desirable to control the location of the end region of the device within the ventricle both with respect to features of the ventricular walls and in relation to other channels formed by the device, and to stabilize the end region of the device within the organ, for example, to counteract reaction forces created by the actuation of the end effector during treatment.

A number of devices are known in the medical arts that provide certain aspects of the desired functionality. For example, U.S. Pat. Nos. 5,389,073 and 5,330,466 to Imran describe steerable catheters; U.S. Pat. No. 5,415,166 to Imran describes a device for endocardial mapping; U.S. Pat. No. 4,813,930 to Elliott describes a radially extendable member for stabilizing an angioplasty catheter within a vessel; U.S. Pat. No. 5,354,310 describes an expandable wire mesh and graft for stabilizing an aneurysm; and U.S. Pat. Nos. 5,358,472 and 5,358,485 to Vance et al. describe atherectomy cutters that provide for aspiration of severed material.

None of the foregoing references overcomes problems associated with locating an end region of a catheter against a position on the inside wall of a heart chamber. Moreover, the prior art is devoid of a comprehensive solution to the above-noted shortcomings of previously-known apparatus for percutaneously performing surgery, and especially for performing TMR.

SUMMARY OF THE INVENTION

In view of the foregoing, it is an object of this invention to provide apparatus and methods for performing surgery, such as TMR, that permit precise control of an end effector disposed in an end region of the apparatus.

It is another object of this invention to provide apparatus and methods, suitable for use in performing TMR and surgery of other hollow-body organs, that include the capability to stabilize within the organ an end region of the device carrying an end effector, for example, to counteract reaction forces created by the end effector during treatment.

These and other objects of the present invention are accomplished by providing apparatus having a directable end region carrying an end effector for performing surgery. Apparatus constructed in accordance with the present invention comprises a catheter having a longitudinal axis and an end region movable to a series of positions along the longitudinal axis. The end region may be selectively moved to a position at an angle relative to the longitudinal axis of the catheter, including a substantially orthogonal position. The catheter includes means for stabilizing a distal region of the apparatus within a hollow-body organ, and for counteracting reaction forces developed during actuation of an end effector.

In a preferred embodiment of the apparatus of the invention, the catheter includes a catheter shaft and a guide member disposed for longitudinal sliding movement within a groove of the catheter shaft. The guide member includes an end region including an end effector maneuverable between a transit position wherein the end region lies parallel to a longitudinal axis of the catheter to a working position wherein the end region and end effector are oriented at an angle relative to the longitudinal axis, including a substantially orthogonal position. The catheter shaft preferably may include adjustable outwardly projecting stabilization members to provide a stable platform to counteract reaction forces generated when the end effector contacts the wall of the hollow-body organ.

Methods of using the apparatus of the present invention to perform surgery, such as transmyocardial revascularization, are also provided.

BRIEF DESCRIPTION OF THE DRAWINGS

Further features of the invention, its nature and various advantages will be more apparent from the accompanying drawings and the following detailed description of the preferred embodiments, in which:

FIG. 7 is a perspective view of the distal region of an alternative embodiment of apparatus constructed in accordance with the present invention;

FIG. 8 is a perspective view of the distal region of the apparatus of the present invention showing an alternative embodiment of the stabilization members;

FIGS. 9A, 9B and 9C are end views, taken along view line 9—9 of FIG. 8, depicting various deployment positions of the stabilization members of FIG. 8;

DETAILED DESCRIPTION OF THE INVENTION

The present invention relates generally to apparatus and methods for percutaneously performing surgery within an organ or vessel. The apparatus of the present invention comprises a catheter including a stabilizing catheter shaft which percutaneously may be disposed within an organ. A guide member engaged with the catheter shaft includes an end region that may be selectively articulated to a position at an angle to a longitudinal axis of the catheter, including a position substantially orthogonal to the longitudinal axis. The end region carries an end effector (e.g., an ablative or mechanical cutting device) for treating tissue. Severed or ablated tissue may be aspirated through the catheter to its proximal end for disposal. The catheter shaft, either alone or in conjunction with stabilizing members, and the guide member, provides precise control over the location of the end region, and thus, the end effector.

The present invention therefore offers a device having a directable end region and end effector for performing surgery that provides a degree of control heretofore unattainable. While the invention is described hereinafter as particularly useful in the emerging field of transmyocardial revascularization, apparatus constructed in accordance with the present invention may be advantageously used in performing surgery on other organs or vessels, such as the intestines, blood vessels or the brain cavities. In addition, while the present invention is described herein in the context of a mechanical cutting system, the control and stabilization apparatus of the present invention may be advantageously used with other types of cutting elements, such as lasers, cryogenic cutters or radio-frequency ablation devices.

Figure 1:
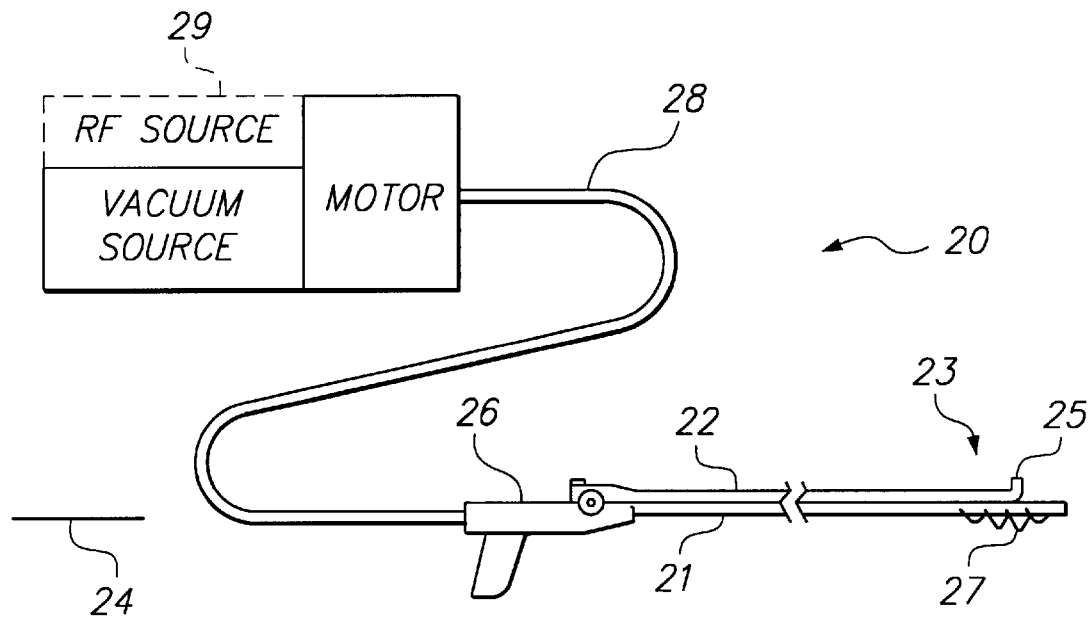
FIG. 1 is a view of a first illustrative embodiment of apparatus constructed in accordance with the present invention.

Referring to FIG. 1, illustrative apparatus 20 constructed in accordance with the present invention is described. Apparatus 20 includes a two-part catheter formed of catheter shaft 21 and guide member 22. Apparatus 20 includes distal region 23 within which guide member 22 has end region 25 that is selectively movable between a transit position parallel to longitudinal axis 24 of catheter shaft 21 and a working position (as shown) substantially orthogonal to longitudinal axis 24. Distal region 23 preferably includes an end effector, described in greater detail hereinbelow, for ablatively or mechanically cutting tissue to attain a treatment goal.

End region 25 of guide member 22 may be positioned longitudinally with respect to catheter shaft 21 by imparting relative movement between guide member 22 and catheter shaft 21 using handle assembly 26. Catheter shaft 21 preferably includes a plurality of stabilizing members 27 to support and stabilize distal region 23 of the apparatus within the hollow-body organ.

Apparatus 20 is coupled via cable 28 to controller 29. In a preferred embodiment wherein the end effector comprises a rotating cutting head, controller 29 includes a motor and control logic for rotating the cutting head responsive to commands input at handle assembly 26 or a footpedal (not shown) and a vacuum source for aspirating severed tissue from the treatment site. Controller 29 optionally may further include RF circuitry (shown in dotted line) for energizing the cutting head to cauterize tissue as it is cut. Alternatively, controller 29 may include a laser source or radio frequency circuitry for causing laser or RF ablation, respectively, using a suitable end effector.

Figure 2:
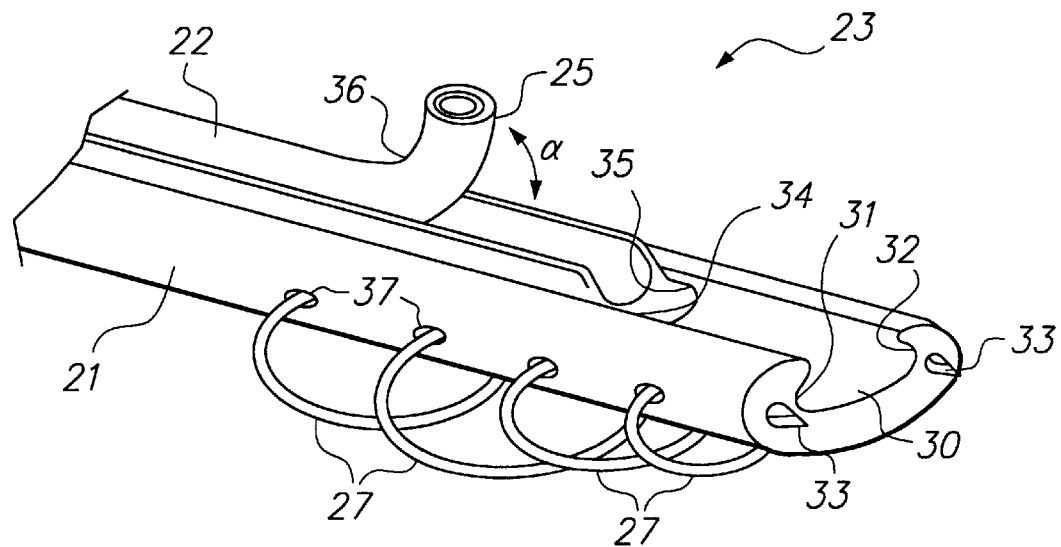
FIG. 2 is a perspective view of the distal region and end effector of the apparatus of FIG. 1.

Referring now to FIGS. 2 and 3, distal region 23 of apparatus 20 is described in greater detail. In FIG. 2, distal region 23 includes end region 25 of guide member 22 disposed in sliding engagement in groove 30 of catheter shaft 21. Catheter shaft 21 may be constructed of a flexible material commonly used in catheter products, such as nylon, polyethylene or polyurethane, and contains lateral grooves 31 and 32 that accept a mating portion of guide member 22 in sliding engagement. Catheter shaft 21 may have an ellipsoidal shape to stabilize the catheter shaft and may include two spaced-apart wire stiffeners that terminate in barbs 33. Barbs 33 are designed to engage an interior surface of an organ, for example, the apex of the left ventricle, to reduce rotation of the catheter shaft when the end effector is actuated. Alternatively, catheter shaft 21 may be formed of a material having sufficient stiffness that the wire stiffeners may be omitted over most of the length of the catheter shaft.

Guide member 22 includes end region 25 carrying an end effector and flanges 34 and 35 that slidingly engage grooves 31 and 32. End region 25 may be articulated in region 36 using control wires or a temperature actuated shape-memory alloy steering mechanism, such as described in the aforementioned patents to Imran. Guide member 22 may be constructed of a spring material (commonly called a Bowden) with spaces in-between the coils to allow it to bend when it is pulled by a control wire asymmetrically, as previously known in the art. Alternatively, guide member 22 may be constructed of a stiffer material such as polyimide coated over a braided steel tubular structure, such as employed in previously known neuro-navigational endoscope devices. In this case, slits are provided on the inside of the bend in region 36 so that the guide member bends in the direction of the slits. The slits allow a tight bend radius which may not otherwise be achievable.

Guide member 22 preferably includes a lumen, as described hereinafter, through which tissue may be evacuated from a treatment site by suction. Accordingly, guide member 22 may also be formed from a loosely wound spring reinforced with a soft elastomeric coating. The elastomeric coating advantageously serves the following functions: it provides sealing along the length of the guide member required to maintain adequate suction through the lumen; it prevents collapse of the lumen in the presence of applied suction; it resists kinking of the coils of the spring; and it also enables the guide member to be bent to relatively tight radii. Reinforced tubing suitable for use as guide member 22 is available from Adam Spence Corporation, Wall, N.J.

In the above-described embodiments, end region 25 of guide member 22 is movable from a transit position lying parallel to the longitudinal axis of catheter shaft 21 to a working position wherein end region 25 is articulated to a position substantially orthogonal to the longitudinal axis of the catheter shaft. In addition, end region 25 may be constructed to enable it to be locked in position at any angle a that may be desired for a given application.

Figure 3A:
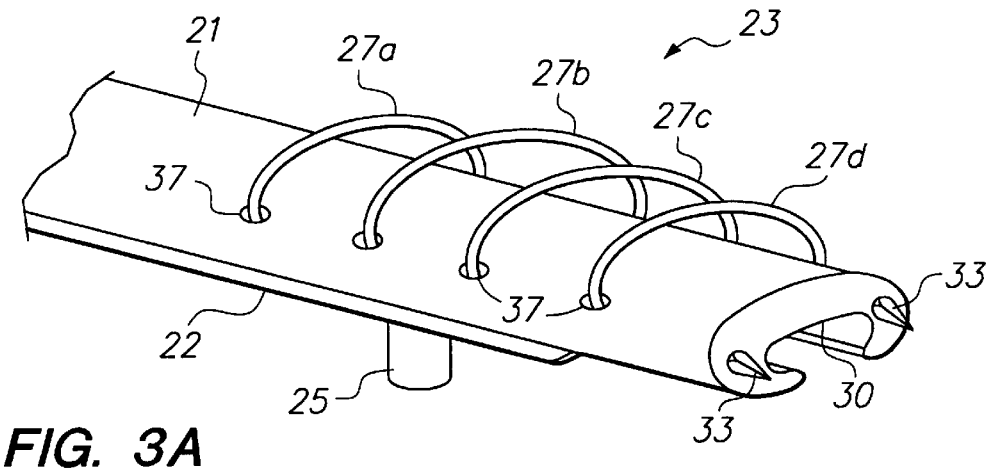
FIGS. 3A and 3B are, respectively, a perspective view and side view of stabilization members disposed on the distal region of the apparatus of FIG. 1.
Figure 3B:
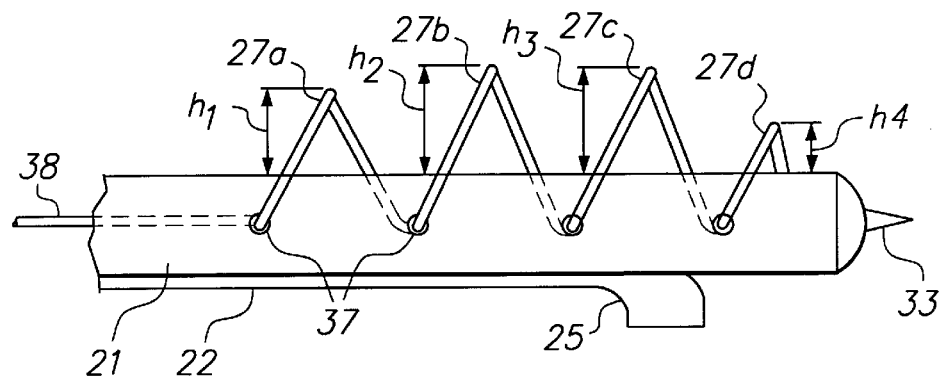

With respect to FIGS. 3A and 3B, stabilization members 27 project outwardly from apertures 37 on either side of catheter shaft 21 in distal region 23. Illustratively, stabilization members 27 comprise four circumferentially-oriented hoops formed of flexible wires 27a–27d. In one preferred embodiment, depicted in FIGS. 3, wires 27a–27d comprise a continuous coil having its distal end affixed to catheter shaft 21 and its proximal end connected to handle assembly 26 via push wire 38. The turns of the coil are slidably disposed in lumens within catheter shaft 21 that interconnect apertures 37 on either side of the catheter shaft. When push wire 38 is urged in the distal direction, wires 27a–27d expands outwards by illustrative distances $h_1$–$h_4$ to contact and conform to the topology of the interior wall of the hollow-body organ or vessel. Wires 27a–27d also may be retracted against catheter shaft 21 by pulling push wire 38 in the proximal direction.

Accordingly, wires 27a–27d may be moved from a retracted position in which they are retracted against distal region 23 of catheter shaft 21 to an expanded position in which they engage a wall of the organ and urge end region 25 into engagement with an opposing wall of the organ, thereby stabilizing catheter shaft 21 against rotation.

Stabilization members 27 may be constructed of any suitable elastic material, including stainless steel, spring steel, nickel-titanium alloys, and a variety of plastics. A nickel-titanium alloy is preferred where wires 27a–27d comprise a continuous coil, as in FIG. 3B. In the contracted mode, catheter shaft 21 and guide member 22 have a relatively small profile, for example, 2–3 mm. Upon actuation of the control means in handle assembly 26, wires 27a–27d expand out as shown in FIG. 3B to form a basket shape that spans and conforms to the lumen of the organ or vessel.

Where stabilization members 27 comprise a single coil, as in FIG. 3B, they may be actuated by a single control means. Alternatively, as described hereinafter with respect to FIG. 8, each of stabilization members 27 may be individually adjusted to conform to the shape of the cavity of the hollow-body organ. Stabilization members 27 may alternatively be oriented parallel to the longitudinal axis of apparatus 20, as described hereinafter with respect to FIG. 8.

The longitudinal position of end region 25 with respect to catheter shaft 21 may be adjusted by sliding guide member 22 in groove 30 of the catheter shaft. Handle assembly 26 preferably includes means, described hereinafter, for moving guide member with respect to catheter shaft 21 so that end region 25 may be positioned at a series of vertical locations. In addition, stabilization members 27 may be adjusted to provide some control over the lateral positioning of the catheter shaft and guide member with respect to the interior wall of the organ or vessel. Thus, apparatus 20 enables a matrix of treatment sites to be accessed without removing and repositioning the apparatus.

Figure 4:
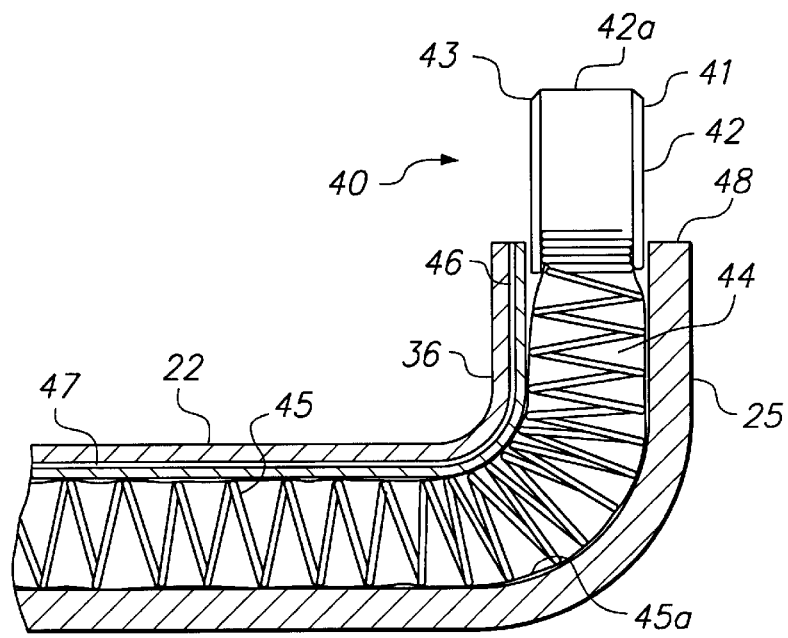
FIG. 4 is sectional view of an illustrative end effector constructed in accordance with the present invention.

Referring now to FIG. 4, end effector 40 (also referred to hereinafter as a "micromorcellator") is described as illustratively comprising a rotary cutting member and drive arrangement. Micromorcellator 40 includes cutting head 41 comprising tubular element 42. Distal edge 42a of tubular element 42 includes a sharpened bevel 43. Cutting head 41 is affixed to drive rod 45, which preferably includes soft plastic or elastomeric coating 45a, as described hereinabove, to maintain suction through lumen 44. The vacuum source in controller 29 aspirates the severed tissue through lumen 44, if provided.

Orientation of end region 25 of guide member 22 is accomplished by control wire 46, which is slidingly disposed in lumen 47 of guide member 22. As described hereinabove, guide member 22 preferably comprises a spring material with spaces in-between the coils to allow it to bend when control wire 46 is retracted in a proximal direction. Alternatively, guide member 22 may be constructed of polyimide coated over a braided steel tube and includes slits on the inside of bend region 36 so that end region 25 bends in the direction of the slits when control wire 46 is retracted in a proximal direction.

Cutting head 41 is connected to the motor of controller 29 via drive rod 45. Drive rod 45 may be formed of a flexible tube such as a bowden or a covered coil or may be formed of a plastic having both high torquability and flexibility. Drive rod 45 is disposed in lumen 44 for a limited range of reciprocation, e.g., up to 3.0 cm, to permit extension of cutting head 41 beyond the end of guide member 22. When end region 25 is in its transit position, cutting head 41 is disposed just below distal endface 48 of guide member 22. Drive rod 45 is hollow and preferably includes a covering of a soft plastic or elastomeric material to allow the application of a negative pressure to aspirate the severed tissue.

Applicant expects that high speed rotation of cutting head 41 will generate frictional heating of the tissue surrounding the cutting head, thereby causing coagulation of the tissue with minimal thermal damage to the surrounding tissue. Alternatively, tubular member 42 of cutting head 41 may comprise an electrically conductive material and be electrically coupled to the optional radio-frequency generator circuitry in controller 29 to provide coagulation of the edges of a channel formed in the tissue by cutting head 41. In this embodiment, tubular element 42 serves as the electrode in a monopolar coagulation arrangement. In addition, a second electrode (not shown) may be formed on the working end spaced apart from the cutting head 41, so that tubular member 42 serves as one electrode of a bipolar coagulation arrangement. Applicant expects that the sealing action produced by RF coagulation, if provided, will simulate the lesions produced by a laser.

Figure 5A:
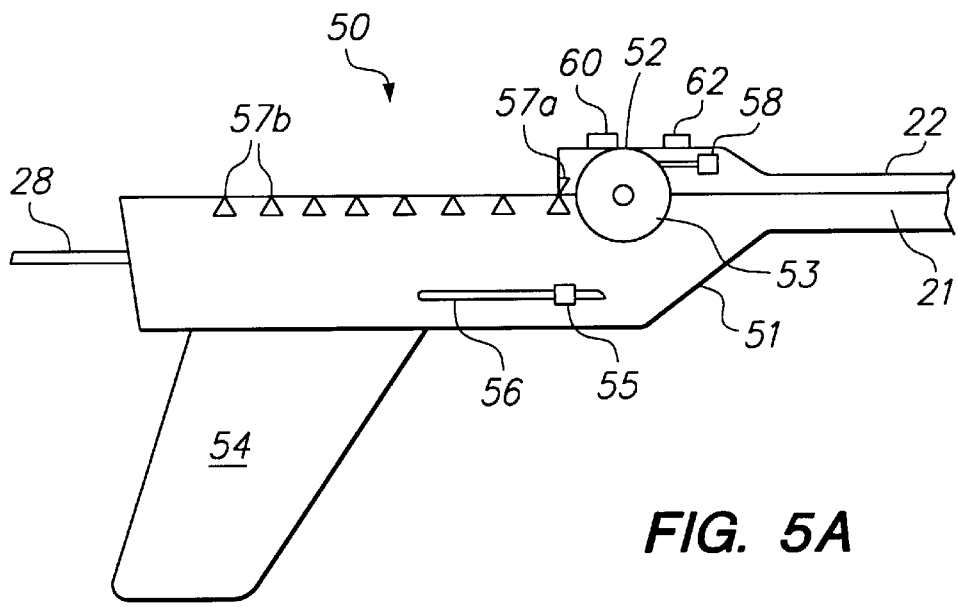
FIGS. 5A and 5B are, respectively, side and perspective views of an illustrative handle assembly for controlling and actuating the apparatus of the present invention.
Figure 5B:
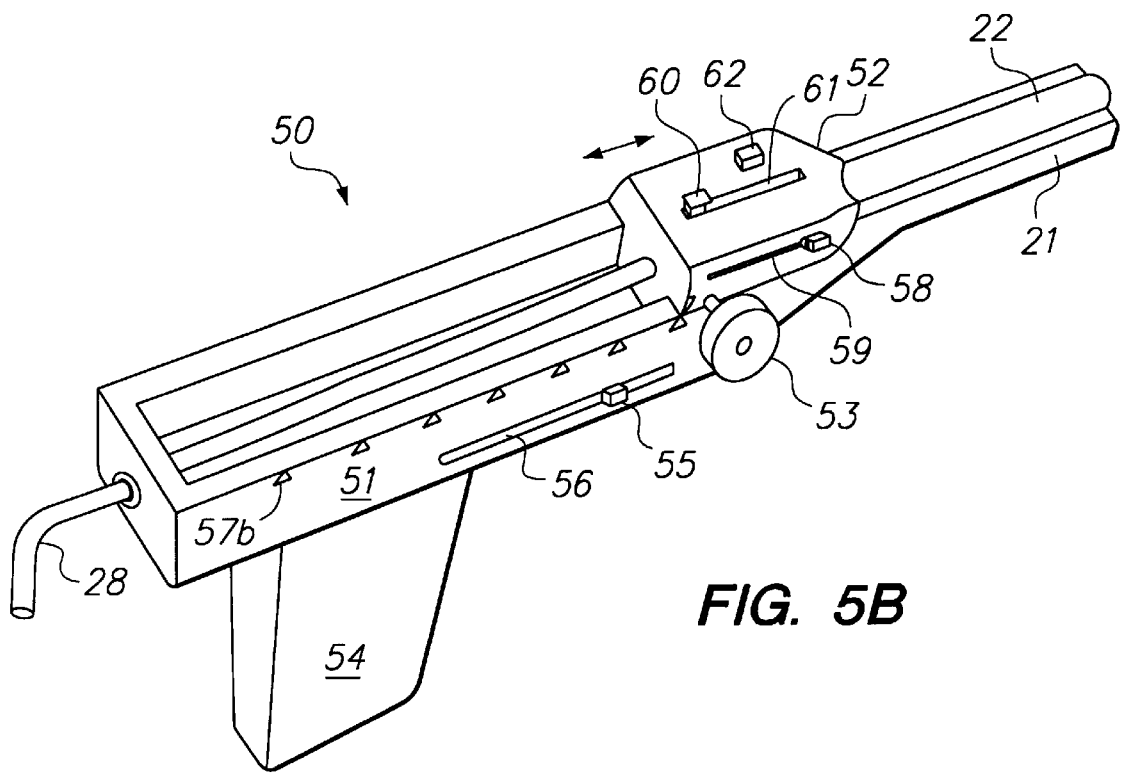

With respect to FIGS. 5A and 5B, illustrative handle assembly 50 is described. Handle assembly 50 includes lower portion 51 affixed to catheter shaft 21 and upper portion 52 affixed to guide member 22. Upper portion 52 is slidingly engaged in lower portion 51, so that guide member 22 may be selectively translated longitudinally with respect to catheter shaft 21 by rotating knob 53. Lower portion 51 of handle assembly 50 includes hand grip 54, and button 55 for controlling the extension of stabilization members 27. Button 55 slides in slot 56 of lower portion 51 to extend or retract stabilization members 27 via push wire 38.

Upper portion 52 includes indicator 57a that may be selectively aligned with indicators 57b, so that the channels formed by end effector 40 are positioned at a series of spaced-apart locations. Cable 28 extends from upper portion 52 and connects the working end of apparatus 20 to controller 29. Upper portion 52 also includes button 58 which may be moved in slot 59 to control the articulation of end region 25 of guide member 22, and depth control lever 60 disposed in slot 61. Depth control lever 60 is moved within slot 61 to control reciprocation of cutting head 41 from end region 25. Slot 61 has a length so that when button 60 is moved to fully extend cutting head 41 from guide member 22, a proximal portion of tubular member 42 remains within guide member 22. In addition, or alternatively, a user-adjustable limit bar (not shown) may be provided in slot 61 to select the maximum extension of cutting head 41 desired for a particular application.

RF button 62 also may be provided to control activation of the optional RF circuitry of controller 29 to coagulate tissue surrounding the channel formed by micromorcellator 40. RF button also could take the form of a microswitch located within slot 61 of handle assembly 50, so as to provide automatic activation of the RF coagulation feature for a short period of time when depth control lever 60 is advanced to contact the user-adjustable limit bar.

It will therefore be seen that handle assembly 50 provides for longitudinal movement of end region 25 with respect to catheter shaft 21 via relative movement between upper portion 52 and lower portion 51 (using knob 53); provides selective deployment of stabilization members 27 via button 55; selective orientation of end region 25 via button 58; control over the depth of the channels formed by end effector 40 via depth control lever 60; and, optionally, activation of an RF coagulation feature via button 62.

Figure 6A:
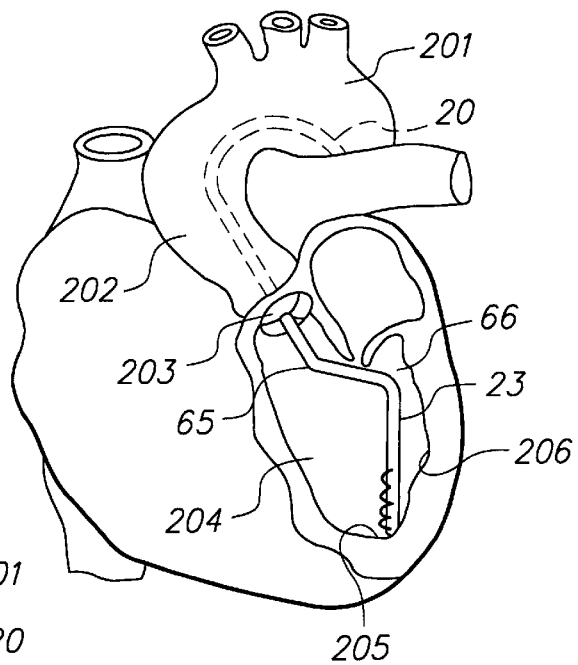
FIGS. 6A–6C are views showing deployment of the apparatus of FIG. 1 in a patient's left ventricle to perform TMR.
Figure 6B:
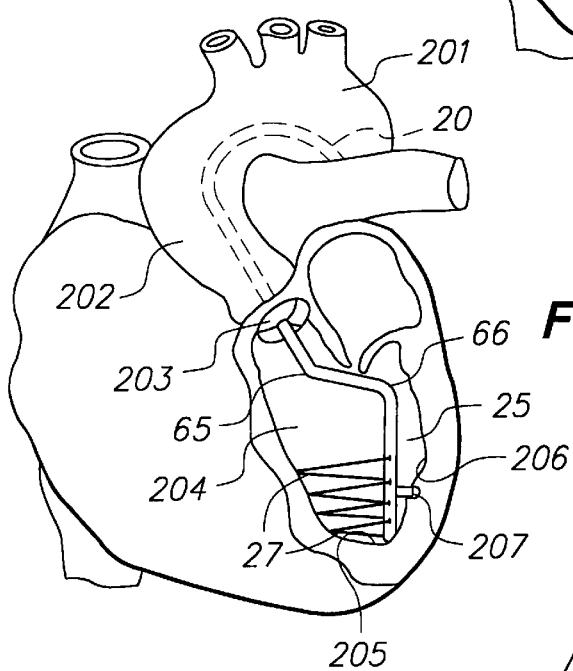
Figure 6C:
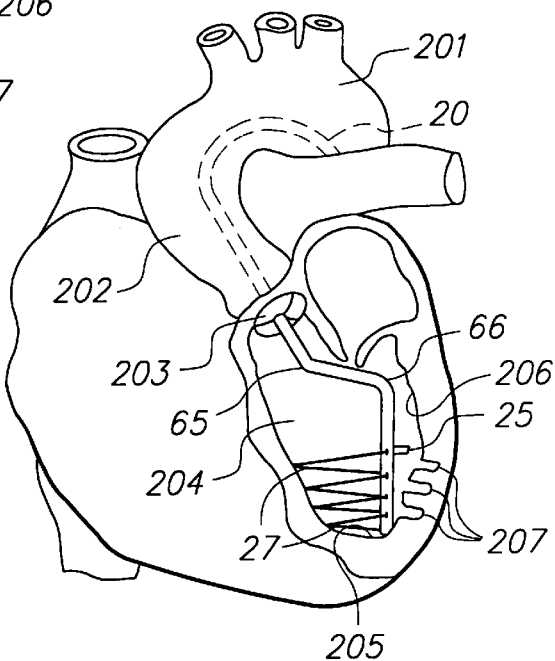

Referring now to FIGS. 6A–6C, operation of apparatus 20 in the context of performing transmyocardial revascularization is described. In FIG. 6A, distal region 23 of apparatus 20 is shown positioned in a patient's left ventricular cavity, using techniques which are per se known. Specifically, distal region 23 of apparatus 20 is inserted via a femoral artery, and is maneuvered under fluoroscopic guidance in a retrograde manner up through the descending aorta, through aortic arch 201, and down through ascending aorta 202 and aortic valve 203 into left ventricle 204. Previously known imaging techniques, such as ultrasound, MRI scan, CT scan, or fluoroscopy, may be used to verify the location of the distal region 23 within the heart.

Insertion of apparatus 20 into the left ventricle is with guide member 22 in its distal-most position with stabilization members 27 fully retracted and end region 25 in its transit position. As barbs 33 of catheter shaft 21 engage apex 205 of the left ventricle, catheter shaft 21 (and guide member 22) preferentially bends in regions 65 and 66 to form a "dog-leg", in which distal region 23 becomes urged against a lateral wall of the ventricle. Regions 65 and 66 where the bends take place may be made flexurally weaker than the remainder of the catheter shaft to aid in the bending of the catheter at these locations.

Referring to FIG. 6B, button 55 is advanced in slot 56 of handle assembly 50 to extend stabilization members 27 so that they engage the septal wall of the left ventricle and urge the end effector against left ventricular wall 206. The dog-leg bends in regions 65 and 66 allow the catheter to be pushed onto the left ventricular wall while the stabilization members push against the septum. End region 25 of guide member 22 is then rotated to its working position by retracting button 58 along slot 59 of handle assembly 50, thus causing end region 25 to be positioned substantially orthogonally to the longitudinal axis of catheter shaft 21.

The motor and vacuum source of controller 29 are then actuated to cause cutting head 41 to rotate and to induce negative pressure in lumen 44 of micromorcellator 40. The clinician then pushes depth control lever 60 distally in slot 61, causing cutting head 41 to be advanced beyond distal endface 48 of guide member 22 and engage the endocardium. When micromorcellator 40 engages the endocardium, a reaction force is generated in catheter shaft 21 that tends both to push end region 25 away from the tissue and to cause the catheter shaft to want to rotate. The relatively flat configuration of catheter shaft 21, in conjunction with barbs 33, is expected to adequately counteract the torque induced by operation of the micromorcellator. In addition, stabilization members 27 function to counteract both these outward reaction and torque effects.

As micromorcellator 40 is advanced to form channel 207 in the left ventricular wall, tissue severed by cutting head 41 is suctioned into lumen 44 and aspirated to the proximal end of apparatus 20 via the vacuum source of controller 29. The depth of channel 207, which is proportional to the movement of depth control lever 60 in slot 61, may be predetermined using conventional ultrasound techniques, MRI scanning, or other suitable methods. As channel 207 is formed, tissue severed from the ventricular wall is aspirated through lumen 44 of guide member 22, thereby reducing the risk of embolization of the severed material. In addition, applicant expects that the use of suction through lumen 44 will assist in stabilizing the micromorcellator, and tend to draw tissue into the cutting head.

Once micromorcellator 40 has achieved its maximum predetermined depth, cutting head 41 is withdrawn from channel 207 by retracting depth control lever 60 to its proximal-most position, thereby returning cutting head 41 to a position just below distal endface 48 of end region 25 of guide member 22. It is expected that rotation of cutting head 41 will generate sufficient frictional heat in the tissue contacting the exterior of cutting head 41 to coagulate the tissue defining the channel.

Optionally, RF button 62 may be depressed on handle assembly 50 to apply a burst of RF energy to the edges of channel 207 as micromorcellator 40 achieves its maximum predetermined depth, and while cutting head 41 is stationary, rotating or being withdrawn from the channel. If provided, this burst of RF energy is expected to further coagulate the tissue defining the walls of channel 207 and modify the surface properties of the tissue.

As shown in FIG. 6C, a series of vertically aligned spaced-apart channels 207 may be formed in left ventricular wall 207 by sliding upper portion 52 proximally within lower portion 51 of handle assembly 50 (by rotating knob 53). Cutting head 41 is then advanced to form a further channel 207 in the tissue, and the tissue may also be coagulated with a burst of RF energy. When upper portion 52 has been retracted to its proximal-most position, button 55 is adjusted as described above with respect to FIGS. 3A and 3B to cause the catheter shaft to rotate several degrees about its axis. Stabilization members 27 are again extended to contact the septal wall, causing micromorcellator 40 to be urged against left ventricular wall 206 in a region laterally spaced apart from the initial line of channels 207.

The foregoing methods enable a matrix of channels to be formed illustratively in the left ventricular wall. It will of course be understood that the same steps may be performed in mirror image to stabilize the apparatus against the left ventricular wall while actuating the end effector to produce a series of channels in the septal region. In accordance with presently accepted theory, the formation of such channels in the endocardium or septal region enables oxygenated blood in the left ventricle to flow directly into the myocardium and thus nourish and oxygenate the muscle. It is believed that these channels may be drilled anywhere on the walls of the heart chamber, including the septum, apex and left ventricular wall, and the above-described apparatus provides this capability.

Referring now to FIG. 7, the distal region of an alternative embodiment of the apparatus of the present invention is described. Apparatus 70 is similar to apparatus 20 described hereinabove, but includes wires 71 and 72 forming a dual-rail on which catheter shaft 73 glides, thereby reducing unwanted rotation of distal region 74 and end region 75. Distal end 76 of the dual-rail includes cushion 77 having barbs 78 for anchoring the catheter shaft in the apex of the left ventricle to prevent inadvertent rotation of catheter shaft 73. Guide member 79 has an inner diameter suitable for carrying one of a variety of end effectors 81, such as a laser fiber, a radio frequency applying device, micromorcellator as described hereinabove, or slit needles, as in the above-mentioned patent to Taheri.

Dual-rail embodiment 70 may be used without stabilization members, or alternatively catheter shaft 73 may include the stabilization members of FIGS. 3 or as described hereinbelow. Wires 71 and 72 also may be formed from a resilient material, e.g., stainless steel or a nickel-titanium alloy, so that when they exit catheter shaft 73 they diverge from one another and give the catheter a larger and more stable base. In this case, cushion 77 preferably comprises an elastomeric material that allows the distance between the tips of wires 71 and 72 to increase beyond the diameter of the catheter. Wires 71 and 72 may have other than circular cross-sections and may take the form of, for example, ribbons.

Wires 71 and 72, in cooperation with a distally-directed axial force exerted on the handle assembly by the clinician, serve to anchor the catheter against a lateral wall of the left ventricle, while catheter shaft 74 and guide member 79 are advanced along the dual-rail. Like apparatus 20, apparatus 70 may include flexurally weaker locations along its length to aid in positioning distal region 74 within the left ventricle.

The dual-rail design of apparatus 70 also may be advantageously employed to determine the location of end region 75 and end effector 81 with respect to the interior of the hollow-body organ or vessel. In this embodiment, wires 71 and 72 are electrically connected within cushion 77 and have a uniform resistance per unit length. Electrodes 80 are positioned in distal end 82 of catheter shaft 73 to measure the resistance of wires 71 and 72 between the electrodes.

The resistance between electrodes 80 may be measured, for example, by ohmmeter circuitry, to determine the distance between the distal end 82 of the catheter shaft and the apex of the left ventricle. In conjunction with the displacement between the upper and lower portions of the handle assembly (see FIGS. 5), the position of end region 75 and end effector 81 may be determined relative to the apex of the heart. This position information may be sampled using suitable analog to digital circuitry, and displayed on a display unit to aid the physician in determining where to place the channels in the heart wall.

Referring now to FIGS. 8 and 9A–9C, a first alternative embodiment of the stabilization members of the present invention are described. In FIG. 8, the distal region of apparatus 90 similar to that of FIG. 1 is shown, in which like components are indicated by like reference numerals. Apparatus 90 includes catheter shaft 21 including barbs 33 and guide member 22 including end region 25. Stabilization members 91a–91d project from proximal apertures 92 and distal apertures 93, and comprise individual longitudinally-oriented flexible wires. Wires 91a–91d enter lumens in catheter shaft 21 through apertures 92 and extend proximally to handle assembly 26. Each of wires 91a–91d preferably has a respective button (similar to button 55 in FIGS. 5) on handle assembly 26 for selectively controlling the extension of the wires.

Accordingly, wires 91a–91d of the embodiment of FIG. 8 may be moved from a retracted position in which they are retracted against distal region 23 of catheter shaft 21 to an expanded position in which they engage a wall of the organ and urge end region 25 into engagement with an opposing wall of the organ, thus stabilizing catheter shaft 21 against rotation.

As illustrated in FIGS. 9A–9B, each of stabilization members 91 preferably may be selectively extended a different amount, therefore causing distal region 23 to rotate about its longitudinal axis. For example, in FIG. 9A, wire 91a is extended from distal region 23 a greater distance, causing a larger bow in wire 91a, while wire 91d is extended a smaller distance, causing a smaller bow therein. Consequently, if each of wires 91a–91d contacts a wall of the organ, catheter shaft 23 will have a tendency to rotate in a counterclockwise direction (viewed from the distal end). Conversely, reversing the extensions of wires 91a and 91d, as in FIG. 9C, will cause rotation in the opposite direction. It is therefore seen that by individually controlling the extension of the stabilization members 91, the position of the catheter with respect to an interior lateral wall of the hollow-body organ can be controlled.

Figure 10:
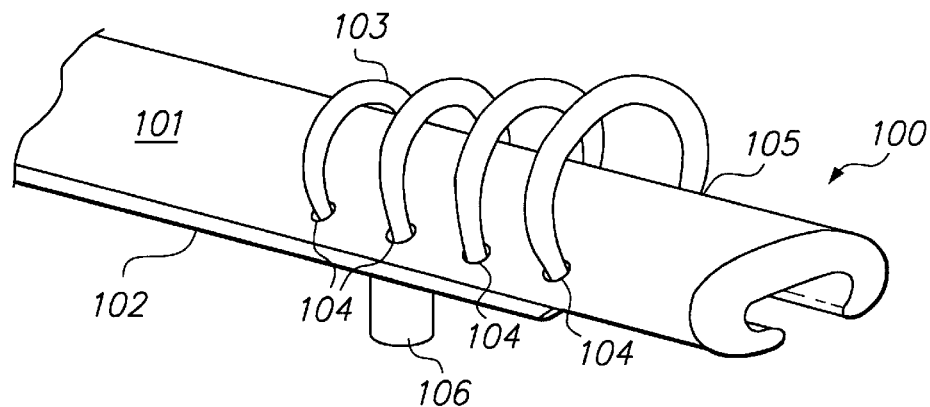
FIG. 10 is a perspective view of the distal region of the apparatus of the present invention showing an alternative embodiment of the stabilization members.
Figure 11:
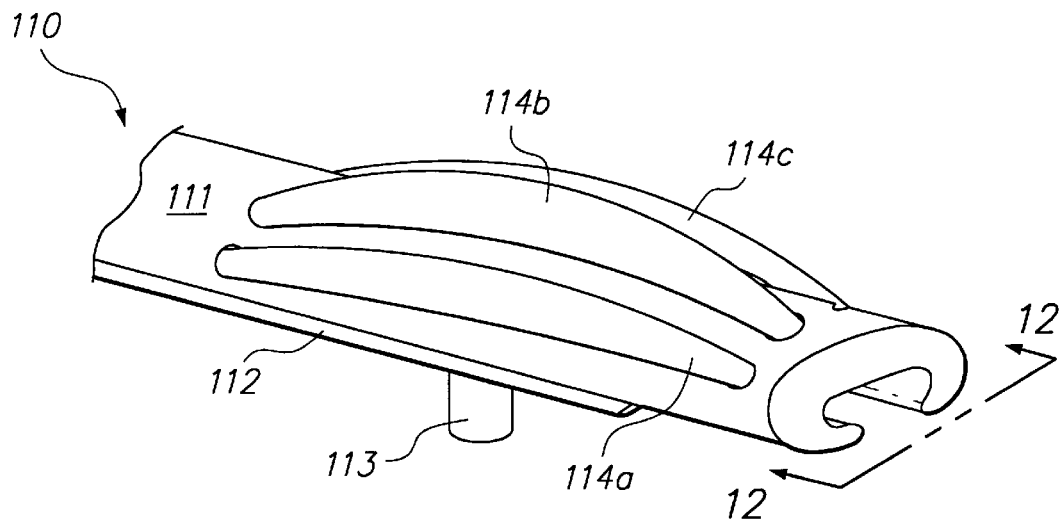
FIG. 11 is a perspective view of the distal region of the apparatus of the present invention showing another alternative embodiment of the stabilization members.

Referring now to FIG. 10 an alternative embodiment of a stabilization arrangement is described. Apparatus 100 includes catheter shaft 101 and guide member 102. Except for stabilization members 103, which in FIG. 10 comprise horizontal inflatable ribs, apparatus 100 is similar to apparatus 20 of FIG. 1.

As described hereinabove, guide member 102 moves relative to catheter shaft 101 to enable the clinician to form a series of vertically aligned channels in the myocardium. Once a line of channels has been formed, the catheter must be moved laterally to a new location and the procedure repeated until the desired number of channels has been achieved. One expedient for doing so, for example, applicable to the apparatus of FIG. 7, is to withdraw the catheter slightly, rotate it and reposition it at a different location on the left ventricular wall. The stabilization arrangement of FIG. 10 instead facilitates lateral movement by deflating ribs 103, rotating catheter shaft 21, and then re-inflating ribs 103.

Specifically, when inflated, stabilization members 103 provide a degree of hoop strength that ensures proper contact of the distal face of end region 106 with the wall of the hollow-body organ or vessel at all times. Once a vertical row of channels has been formed, stabilization members 103 are deflated by the clinician and end region 106 is moved to a new lateral position. The stabilization members are fully re-inflated and another vertical row of channels is formed, as discussed hereinabove.

Figure 12A:
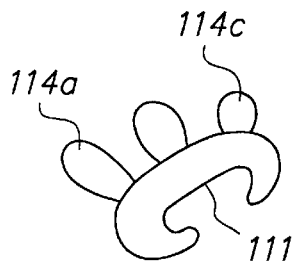
FIGS. 12A–12C are end views, taken along view line 12—12 of FIG. 11, depicting various deployment positions of the stabilization members of FIG. 11.
Figure 12B:
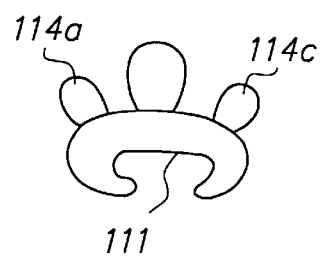
Figure 12C:
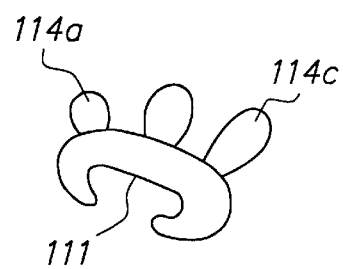

With respect to FIGS. 11 and 12A–12C, another embodiment of the apparatus of the present invention is described in which the stabilization members comprise longitudinally-oriented balloons. Apparatus 110 is otherwise similar to the apparatus of FIG. 8, and includes catheter shaft 111, guide member 112, and end region 113. Stabilization elements 114a–114c comprise balloons, preferably formed of a compliant material, such as polyurethane, silicone or latex. The handle assembly for apparatus 110 includes valving means for selectively individually inflating balloons 114a–114c. As shown in FIGS. 12A–12C, balloons 114a–114c may be selectively inflated via inflation lumens (not shown) in catheter shaft 111 to stabilize apparatus 110 within a hollow-body organ, and to rotate catheter shaft 111 (and end region 113) in a manner similar to that described above with respect to FIGS. 9A–9C.

Figure 13:
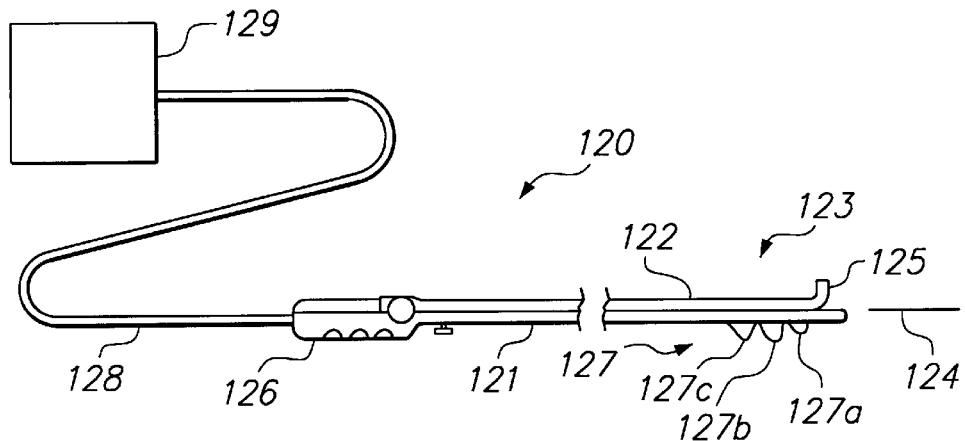
FIG. 13 is a view of an alternative embodiment of apparatus constructed in accordance with the present invention.

Referring now to FIG. 13, a further alternative embodiment of apparatus constructed in accordance with the present invention is described. Apparatus 120 comprises a two-part catheter formed of catheter shaft 121 and guide member 122. Apparatus 120 includes distal region 123 within which guide member 122 has end region 125 that is selectively movable between a transit position parallel to longitudinal axis 124 of catheter shaft 121 and a working position (as shown), substantially orthogonal to longitudinal axis 124. Distal region 123 preferably includes an end effector, as described in detail hereinabove.

End region 125 of guide member 122 may be positioned longitudinally with respect to catheter shaft 121 by imparting relative movement between guide member 122 and catheter shaft 121 using handle assembly 126. Catheter shaft 121 includes stabilizing assembly 127 to support and stabilize distal region 123 of the apparatus within an organ or vessel.

Apparatus 120 is coupled via cable 128 to controller 129. In a preferred embodiment, wherein the end effector comprises a flexible wire having a sharpened tip, controller 129 includes a hydraulic or pneumatic piston, valve assembly and control logic for extending and retracting the end effector beyond the distal endface of end region 125 responsive to commands input at handle assembly 126 or a footpedal (not shown). Controller 129 optionally may further contain RF generator circuitry for energizing electrodes disposed on the end effector to cause a controlled degree of necrosis at the treatment site.

Figure 14A:
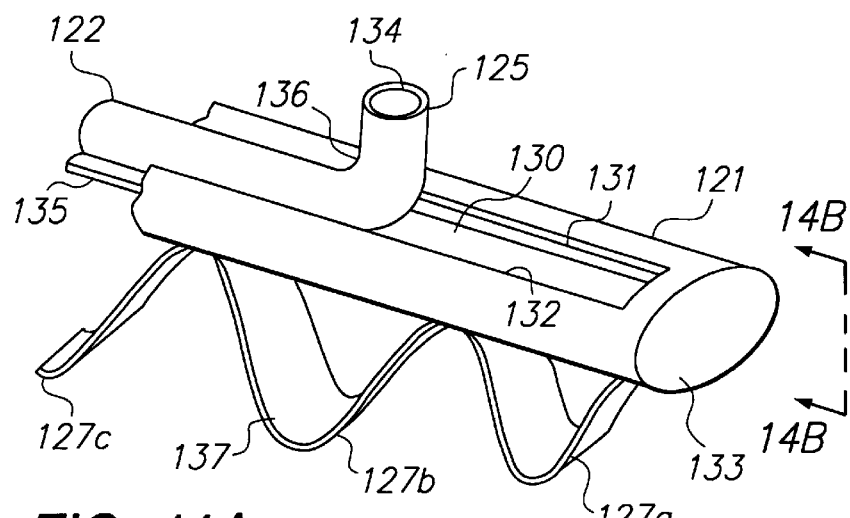
FIGS. 14A and 14B are, respectively, perspective top and bottom views of a distal region of the apparatus of FIG. 13.
Figure 14B:
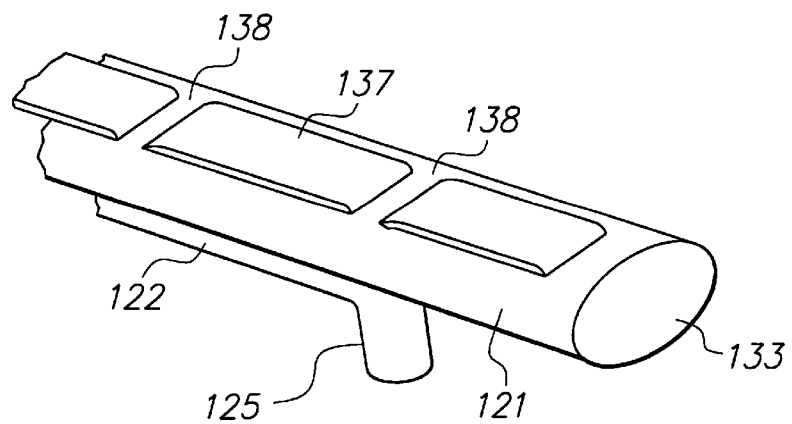

Referring now to FIGS. 14A and 14B, distal region 123 of apparatus 120 is described in greater detail. In FIG. 14A, distal region 123 includes end region 125 of guide member 122 disposed in sliding engagement in track 130 of catheter shaft 121, as described hereinabove with respect to the embodiment of FIG. 1. Guide member 122 includes end region 125 carrying end effector 134 and flanges 135 that slidingly engage grooves 131 and 132. End region 125 may be articulated in region 136 using control wires or a temperature actuated shape-memory alloy steering mechanism, as described hereinabove.

End region 125 of guide member 122 is movable from a transit position lying parallel to longitudinal axis 124 of catheter shaft 121 to a working position wherein end region 125 is articulated to a position substantially orthogonal to the longitudinal axis of the catheter shaft. In addition, end region 125 may be constructed to enable it to be locked in position at any angle α that may be desired for a given application.

Stabilization assembly 127 comprises flat band 137 of resilient material, such as stainless steel, that projects outwardly from catheter shaft 121 in distal region 123. Illustratively, stabilization assembly 127 comprises multiple loops 127a–127c of band 137. Band 137 has its distal end affixed to the distal end of catheter shaft 121, and its proximal end connected to handle assembly 126. Band 137 passes through an interior lumen of catheter shaft 121 (see FIG. 15) and exits to the exterior surface of catheter shaft 121 in distal region 123. Crossbars 138 permit band 137 to be pulled flat against the exterior surface of catheter shaft 121, as shown in FIG. 14B, or urged in a distal direction to form loops 127a–127c.

Figure 15:
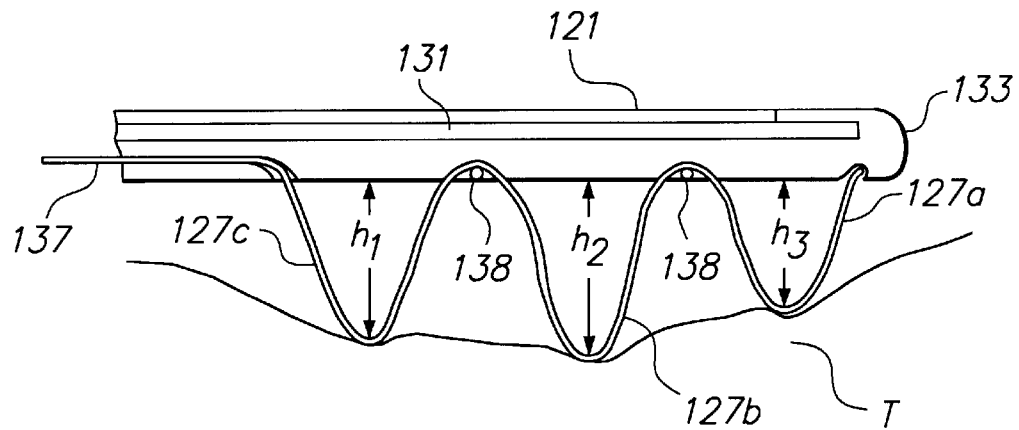
FIG. 15 is a partial side view, partly in section, of the catheter shaft of FIGS. 13 and 14 deployed in contact with tissue.

Referring to FIG. 15, in which guide member 122 is omitted for clarity, when the proximal end of band 137 is urged in the distal direction, loops 127a–127c expand outwardly by illustrative distances $h_1$–$h_3$ to contact and conform to the topology of interior wall T of an organ or vessel.

Accordingly, loops 127a–127c may be moved from a retracted position in which they are retracted against an exterior surface of distal region 123 of catheter shaft 121 (FIG. 14B) to an expanded position (FIG. 14A) in which they engage a wall of an organ or vessel.

In the position shown in FIG. 14A, stabilization assembly 127 urges end region 125 into engagement with an opposing wall of the organ, thereby stabilizing catheter shaft 121 against rotation. Band 137 may be constructed of any suitable elastic material, including stainless steel, spring steel, nickel-titanium alloys, and a variety of plastics. In the contracted mode, catheter shaft 121 and guide member 122 have a relatively small profile, for example, 2–3 mm.

The longitudinal position of end region 125 with respect to catheter shaft 121 may be adjusted by sliding guide member 122 in track 130 of the catheter shaft. Handle assembly 126 preferably includes means, described hereinafter, for moving guide member 122 with respect to catheter shaft 121 so that end region 125 may be positioned at a series of longitudinal locations. In addition, stabilization assembly 127 may be adjusted to provide some control over the lateral positioning of the catheter shaft and guide member with respect to the interior wall of the organ or vessel. Thus, apparatus 120 enables a matrix of treatment sites to be accessed without removing and repositioning the apparatus.

With respect to FIG. 8, illustrative handle assembly 126 is described. Handle assembly 126 includes lower portion 140 affixed to catheter shaft 121 and upper portion 141 affixed to guide member 122. Upper portion 141 is slidingly engaged in lower portion 140, so that guide member 122 may be selectively translated longitudinally with respect to catheter shaft 121 by rotating knob 142. Upper portion 141 includes ribbed bonnet 143, which collapses and expands to enclose lower portion 140 as upper portion 141 is moved in the proximal and distal directions, respectively. Lower portion 140 of handle assembly 126 includes indentations 144 forming a hand grip.

Figure 16:
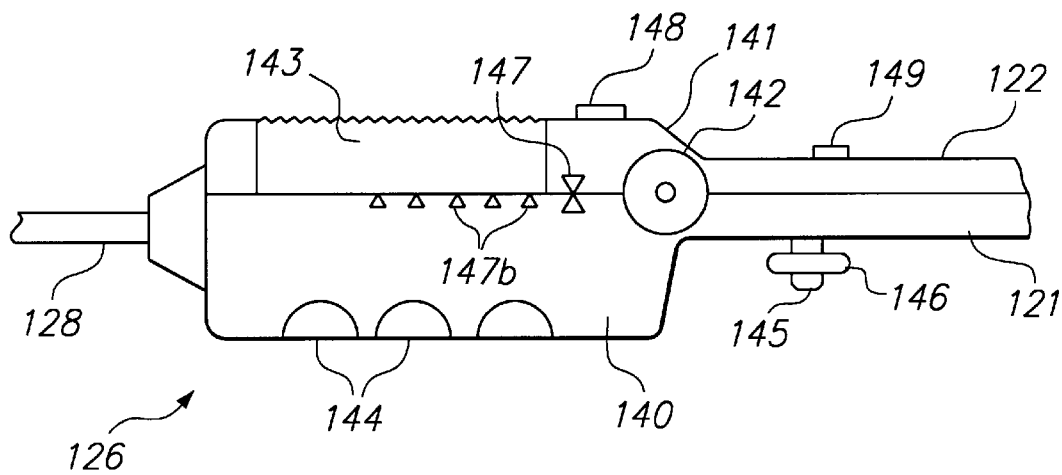
FIG. 16 is a side view of the handle portion of the apparatus of FIG. 13.

Threaded post 145 is coupled to the proximal end of band 137, and slides in a slot (not visible in FIG. 16) in the lower surface of catheter shaft 121. Thumbwheel 146 is threaded onto post 145. Post 145 and thumbwheel 146 permit the proximal end of band 137 (see FIG. 15) to be urged in the proximal and distal directions, for example, to deploy stabilization assembly 127. Band 137 then is locked into position by tightening thumbwheel 146 on post 145 against the lower surface of catheter shaft 121.

Upper portion 141 includes indicator 147a that may be selectively aligned with indicators 147b, so that the treatment sites are positioned at a series of spaced-apart locations. Cable 128 extends from upper portion 141 and connects the end effector of apparatus 120 to controller 129. Button 148 disposed on the top surface of upper portion 141 may be depressed to command the control logic of controller 129 to reciprocate the end effector from end region 125, and optionally, cause necrosis at the treatment site. Button 149, disposed in a slot in the upper surface of the proximal end of guide tube 122 (not visible in FIG. 16) is coupled to a tendon affixed to end region 125, and may be moved in the proximal and distal directions to control the degree of articulation of end region 125 and the end effector.

Handle assembly 126 therefore provides for longitudinal movement of end region 125 with respect to catheter shaft 121 via relative movement between upper portion 141 and lower portion 140 (using knob 142); provides selective deployment of stabilization assembly 127 (using post 145 and thumbwheel 146); selective orientation of end region 125 (using button 149); and control over operation of the end effector (using button 148).

Figure 17A:
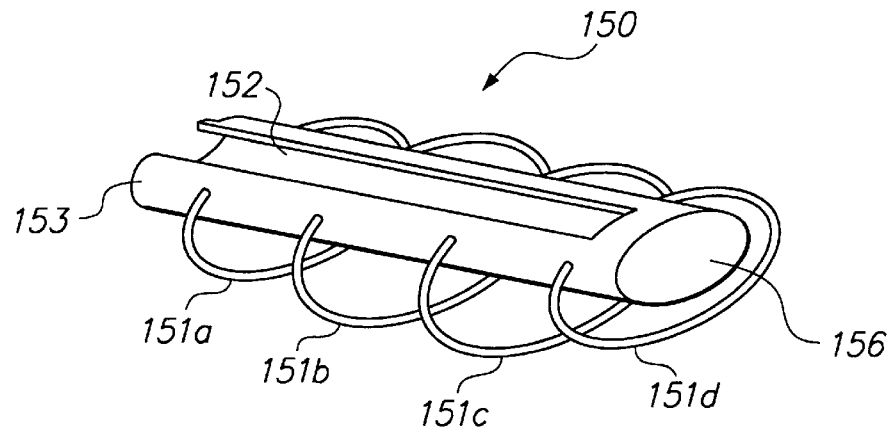
FIGS. 17A and 17B are, respectively, top and side sectional views of the distal region of an alternative embodiment of the apparatus of the present invention.
Figure 17B:
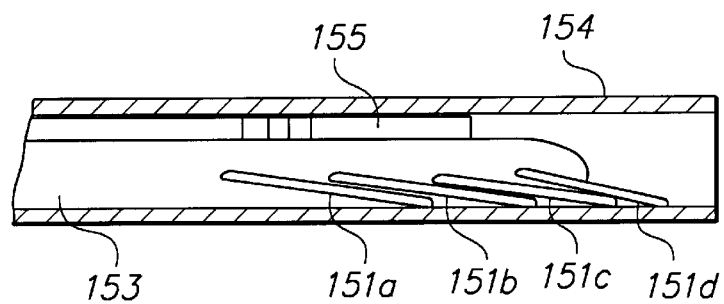

Referring now to FIGS. 17A and 17B, a yet further alternative embodiment of the stabilization assembly of the apparatus of the present invention is described. Apparatus 150 is similar to apparatus 120 described hereinabove, but band 137 that forms stabilization assembly 127 of apparatus 120 is replaced by transversely mounted fixed wire hoops 151a–151d. In FIG. 17A, the guide catheter is omitted from track 152 for clarity. Wire hoops 151a–151d, illustratively four in number, have their ends affixed to the lateral faces of catheter shaft 153 so that, when unconstrained, the hoops return to a position substantially orthogonal to the longitudinal axis of catheter shaft 153. Wire hoops preferably comprise a sturdy, elastic plastic or metal alloy, such as nickel-titanium.

In FIG. 17B, catheter shaft 153 is shown disposed within outer sheath 154. When retracted within outer sheath 154, hoops 151a–151d are deformed so that they lie adjacent to the exterior surface of catheter shaft 153. Guide member 155 and catheter shaft 153 are delivered to the left ventricle while enclosed within outer sheath 154. Once distal endface 156 is positioned against the apex of the left ventricle, for example, as determined by fluoroscopy, outer sheath 154 is retracted proximally. This permits hoops 151a–151d to resume their preferred shape, and urge guide member 155 against the opposing wall of the left ventricle. Hoops 151a–151d serve to stabilize and counteract reaction forces generated by operation of the end effector.

Figure 18:
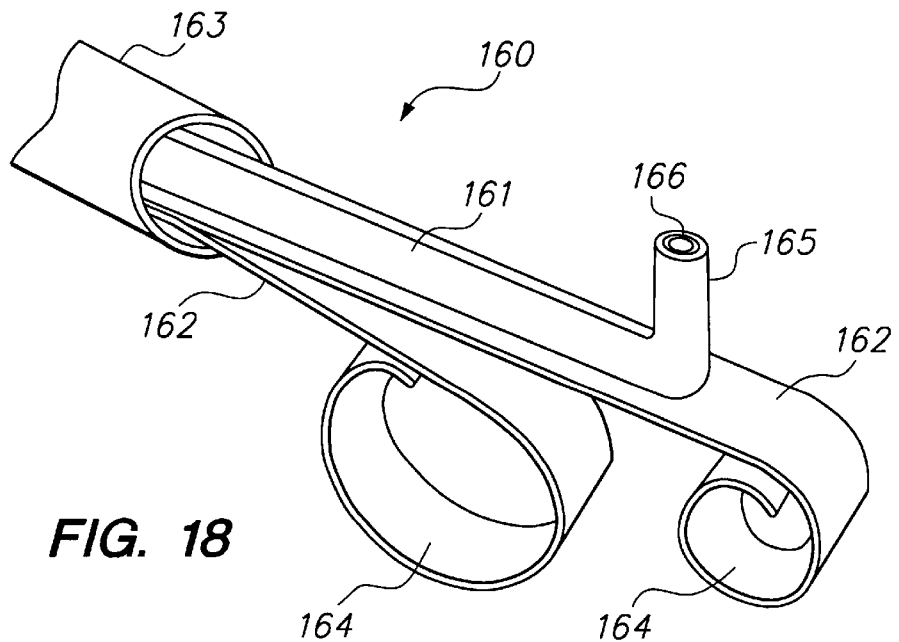
FIG. 18 is a perspective top view of the distal region of a further alternative embodiment of the apparatus of the present invention.

With respect to FIG. 18, a still further alternative embodiment of the stabilization assembly of the present invention is described. In apparatus 160 of FIG. 18, the catheter shaft is omitted, and guide member 161 is supported by a plurality of bands 162 (only two are shown in FIG. 18). Guide member 161 and bands 162 extend from within outer sheath 163. Each band 162 preferably terminates in spool 164 when it is extended from within outer sheath 163. Spools 164 contact one wall of the organ or vessel and urge end region 165 of guide member 161 into contact with the opposing wall of the organ or vessel. Preferably, the length of each band 162 may be adjusted using suitable means disposed on the handle assembly. Operation of guide member 161 and end effector 166 are the same as described herein for other embodiments of the present invention.

Figure 19:
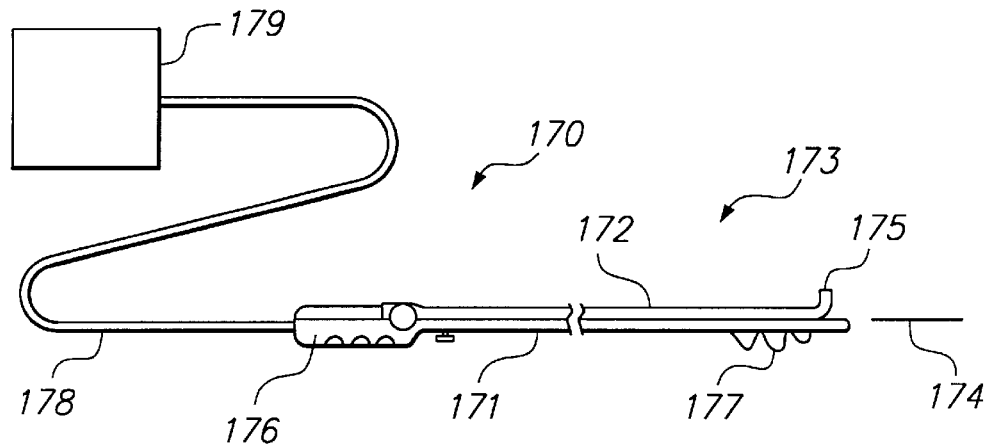
FIG. 19 is a view of a further alternative embodiment of apparatus of the present invention.

Referring to FIGS. 19 and 20, another embodiment of apparatus of the present invention is described. Apparatus 170 comprises a two-part catheter formed of catheter shaft 171 and guide member 172, and is coupled via cable 178 to controller 179 that performs the functions described above with respect to controller 129 of the embodiment of FIG. 13.

Apparatus 170 includes distal region 173 within which guide member 172 has end region 175 that is selectively movable between a transit position parallel to longitudinal axis 174 of catheter shaft 171 and a working position (as shown), substantially orthogonal to longitudinal axis 174. Distal region 173 preferably includes an end effector, as described in detail hereinabove. End region 175 of guide member 172 may be positioned longitudinally with respect to catheter shaft 171 by imparting relative movement between guide member 172 and catheter shaft 171 using handle assembly 176. Catheter shaft 121 includes stabilizing element 177 to support and stabilize distal region 173 of the apparatus within an organ or vessel.

Figure 20A:
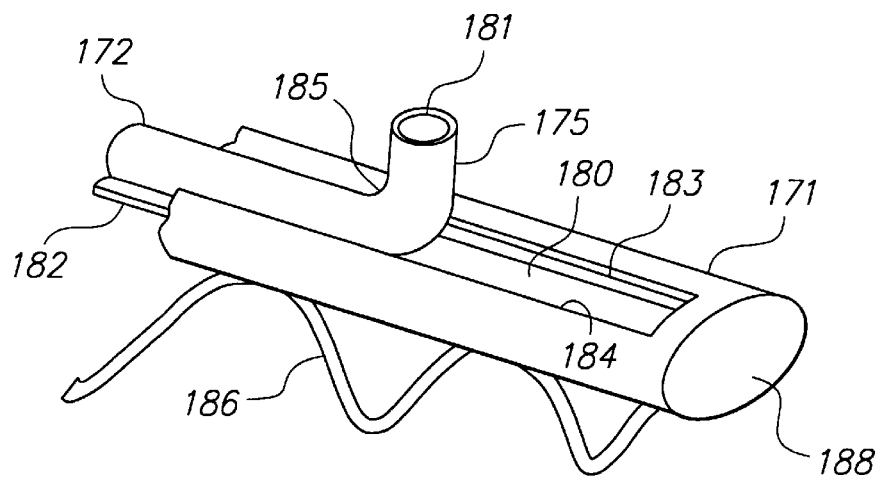
FIGS. 20A and 20B are, respectively, perspective top and side views of a distal region of the apparatus of FIG. 19.
Figure 20B:
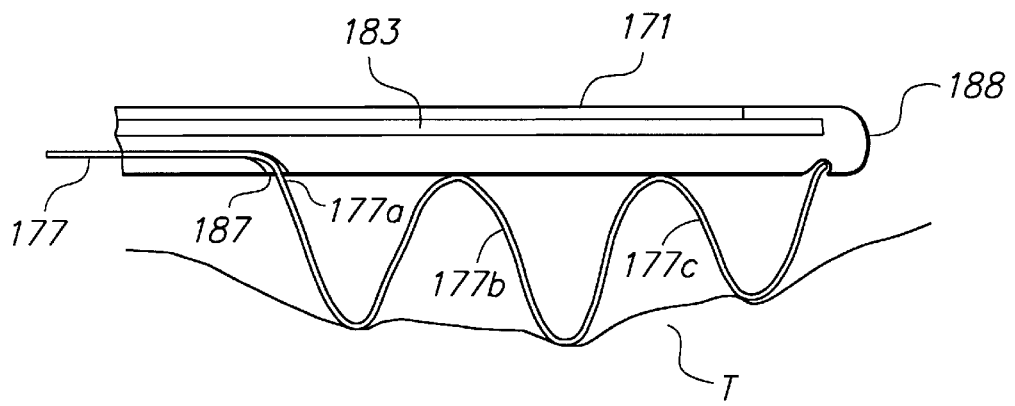

Distal region 173 of apparatus 170 is described in greater detail with respect to FIGS. 20A and 20B. Distal region 173 includes end region 175 of guide member 172 disposed in sliding engagement in track 180 of catheter shaft 171, as described hereinabove with respect to other embodiments. Guide member 172 includes end region 175 carrying end effector 181 and flanges 182 that slidingly engage grooves 183 and 184. End region 175 may be articulated in region 185, as may be constructed and operated as described hereinabove for other embodiments.

Stabilization element 177 comprises wire or band 186 of resilient material, such as stainless steel, that exits catheter shaft 171 through skive 187, and is fixed to catheter shaft 171 near distal end 188. When deployed within a hollow organ, such as a chamber of the heart, as depicted in FIG. 20B, stabilization element 177 forms a plurality of sinusoidal bends 177a–177c that support distal end 173 of catheter shaft 171. Stabilization element 177 preferably comprises a material having a shape-memory and that is capable of reforming to a desired shape when extended through skive 187.

While preferred illustrative embodiments of the invention are described, it will be apparent to one skilled in the art that various changes and modifications may be made without departing from the invention, and the appended claims are intended to cover all such changes and modifications that fall within the true spirit and scope of the invention.

What is claimed is:

1. Apparatus for treating an organ or vessel defining a cavity, the apparatus comprising:

a catheter shaft adapted for insertion into the cavity, the catheter shaft having a distal region and a portion defining a groove, a guide member including an end effector to treat an interior wall of the hollow-body organ, the guide member disposed in the groove for translation along the catheter shaft;

means for disposing the end effector at a selected orientation relative to the catheter shaft; and a stabilization assembly, disposed in the distal region, that stabilizes the catheter shaft and guide member within the organ or vessel during actuation of the end effector.

2. The apparatus as defined in claim 1 wherein the stabilization assembly comprises a band movable from a first position, wherein the band is disposed adjacent to an exterior surface of the catheter shaft, to a second position, wherein the band forms a plurality of loops extending from the exterior surface of the catheter shaft.

3. The apparatus as defined in claim 1 wherein the end effector comprises a rotating cutting head.

4. The apparatus as defined in claim 3 wherein the end effector further comprises an electrode adapted to deliver RF energy.

5. The apparatus as defined in claim 1 wherein the apparatus further comprises an outer sheath and the stabilization assembly comprises a plurality of wire hoops affixed to the catheter shaft, the plurality of wire hoops movable from a first position wherein the wire hoops are confined within the outer sheath, and a second position, wherein the wire hoops project outwardly from the catheter shaft to engage an interior surface of the organ or vessel.

6. The apparatus as defined in claim 5 wherein the end effector comprises a rotating cutting head.

7. The apparatus as defined in claim 6 wherein the end effector further comprises an electrode adapted to deliver RF energy.

8. Apparatus for treating an organ or vessel comprising:
   an outer sheath;
   a guide member extending from the outer sheath, the guide member including an end effector for treating an interior region of an organ or vessel, an end region of the guide catheter movable to dispose the end effector at a selected orientation relative to the catheter shaft; and a stabilization assembly comprising a plurality of bands extending from within the outer sheath, each one of the plurality of bands terminating in a spool that contacts an interior wall of the organ or vessel, the stabilization assembly stabilizing the guide member during actuation of the end effector.

9. The apparatus as defined in claim 8 wherein the end effector further comprises an electrode adapted to deliver RF energy to the treatment site.

10. Apparatus for performing transmyocardial revascularization, the apparatus comprising:

a catheter shaft adapted for insertion into a patient's left ventricle, the catheter shaft having a distal region including a portion adapted to engage an interior wall in a vicinity of an apex of the patient's left ventricle;

a guide member having an end effector to treat the interior wall of the left ventricle, the guide member disposed for translation along the catheter shaft; and a stabilization assembly, disposed in the distal region, that stabilizes the catheter shaft and guide member within the left ventricle during actuation of the end effector.

11. The apparatus as defined in claim 10 wherein the stabilization assembly comprises a band movable from a first position, wherein the band is disposed adjacent to an exterior surface of the catheter shaft, to a second position, wherein the band forms a plurality of loops extending from the exterior surface of the catheter shaft.

12. The apparatus as defined in claim 10 wherein the stabilization assembly comprises a wire movable from a first position, wherein the wire is partially retracted within a lumen of the catheter shaft, to a second position, wherein the wire forms a plurality of bends that contact and support the catheter shaft.

13. The apparatus as defined in claim 10 wherein the end effector comprises a rotating cutting head.

14. The apparatus as defined in claim 12 wherein the end effector further comprises an electrode adapted to deliver RF energy.

15. A method of treating an interior region of an organ or vessel comprising:

providing apparatus having a catheter shaft adapted for insertion into an organ or vessel, a guide member mounted in a groove on the catheter shaft and having an end effector for treating an interior region of the organ or vessel, and a stabilization assembly mounted on the catheter shaft;

inserting the apparatus within an organ or vessel;

deploying the stabilization assembly to stabilize the catheter shaft and guide member within the organ or vessel;

translating the guide member within the groove of the catheter shaft to dispose the end effector at a selected location relative to the catheter shaft; and actuating the end effector to form a channel in an interior region of the organ or vessel.

16. The method as defined in claim 15 further comprising delivering RF energy to the channel to create a controlled depth of necrosis.

17. The method as defined in claim 15 further comprising, following actuating the end effector:

translating the guide member in the groove relative to the catheter shaft to relocate the end effector; and repeating actuation of the end effector.

18. The method as defined in claim 15 wherein the stabilization assembly comprises a band movable from a first position, wherein the band is disposed adjacent to an exterior surface of the catheter shaft, to a second position, wherein the band forms a plurality of loops extending from the exterior surface of the catheter shaft, and deploying the stabilization assembly to stabilize the catheter shaft and guide member within the organ or vessel further comprises moving the band from the first position to the second position.

19. The method as defined in claim 15 wherein actuating the end effector comprises rotating a cutting head.

20. The method as defined in claim 15 wherein the stabilization assembly comprises a plurality of wire hoops affixed to the catheter shaft, the plurality of wire hoops movable from a first position wherein the wire hoops are confined within the outer sheath, and a second position, wherein the wire hoops project outwardly from the catheter shaft to engage an interior surface of the organ or vessel, and deploying the stabilization assembly to stabilize the catheter shaft and guide member within the organ or vessel further comprises retracting the outer sheath.

21. The method as defined in claim 15 wherein the stabilization assembly comprises a wire movable from a first position wherein the wire is partially retracted within the catheter shaft, and a second position, wherein the wire forms a plurality of interconnected bends that engage an interior surface of the organ or vessel, and deploying the stabilization assembly to stabilize the catheter shaft and guide member within the organ or vessel further comprises extending the wire so that it resumes a preformed shape.

22. A method of treating an interior region of an organ or vessel comprising:

providing apparatus having an outer sheath, a guide member extending from the outer sheath, the guide member including an end effector for treating an interior region of the organ or vessel; and a stabilization assembly comprising a plurality of bands extendable from within the outer sheath, each one of the plurality of bands terminating in a spool that contacts an interior wall of the organ or vessel when extended;

inserting the apparatus within an organ or vessel;

extending the plurality of bands from the outer sheath to form spools, each spool contacting an interior wall of the organ or vessel to stabilize the guide member within the organ or vessel;

translating the guide member to dispose the end effector at a selected location; and actuating the end effector to form a channel in an interior region of the organ or vessel.

* * * * *